United States Patent [19]

Quinkert et al.

[11] 4,357,278

[45] Nov. 2, 1982

[54] PROCESS FOR SYNTHESIZING ESTRONE OR ESTRONE DERIVATIVES

[75] Inventors: Gerhard Quinkert, Glasshütten; Wolf-Dietrich Weber; Ulrich Schwartz, both of Frankfurt am Main, all of Fed. Rep. of Germany

[73] Assignee: Hoechst Aktiengesellschaft, Frankfurt am Main, Fed. Rep. of Germany

[21] Appl. No.: 252,841

[22] Filed: Apr. 10, 1981

[30] Foreign Application Priority Data

Apr. 12, 1980 [DE] Fed. Rep. of Germany ....... 3014120

[51] Int. Cl.$^3$ ................................................. C07J 1/00
[52] U.S. Cl. ............................ 260/397.45; 560/122; 568/314; 568/315; 568/330
[58] Field of Search ............................ 260/586, 397.45

[56] References Cited

U.S. PATENT DOCUMENTS 4,029,648   6/1977   Ponsold et al. ............ 260/239.55 R

FOREIGN PATENT DOCUMENTS 2523179   5/1976   Fed. Rep. of Germany ........................ 260/239.55

OTHER PUBLICATIONS

Chem. Abstr. 75, 77122x, (1971).
J. Am. Chem. Soc. 99, 3461–3466, (1977).
Chemical Abstracts, vol. 75, (1971, Pars 77,122x.

*Primary Examiner*—Elbert L. Roberts
*Attorney, Agent, or Firm*—Curtis, Morris & Safford

[57] ABSTRACT

What are disclosed are a multi-step synthesis for the preparation of 9(11)-dehydroestrone 3-methyl ether from 2-methyl,4-methoxy benzaldehyde; 1-(4-methoxy-2-methyl-(phenyl)-3-(1-methyl-2-oxo-5-t-vinyl-cyclopent-r-yl)-propane-1-one, an intermediate in said synthesis; and a method for the preparation of 3-vinylcyclopentanone from 2-vinylcyclopropane-1,1-dicarboxylic acid.

3 Claims, No Drawings

PROCESS FOR SYNTHESIZING ESTRONE OR ESTRONE DERIVATIVES

The invention relates to a process for synthesizing estrone or estrone derivatives which, if appropriate, contain a 10-α-hydroxyl group or a 9(11) double bond.

Derivatives of, and chemical variants of, the steroid follicular hormone (estrogen) play an important part in practical gynecology as potent active compounds in the female sexual cycle or as an important component in oral hormone contraceptives. In addition, the said estrogens are important (chemical) starting products or intermediate products for conversion by chemical means into 19-nor-steroids (gonane derivatives). In the form of their numerous chemical and structural variants, the latter are also of great practical interest for the treatment of a variety of disturbed sexual functions or as a further component of oral hormone contraceptives.

Previously, estrogens were prepared on an industrial scale mainly from the plant steroid saponin diosgenin. In recent times, as a consequence of the worldwide increase in price and scarcity of the vegetable starting material, there has been a shift in industrial production towards the total synthesis of this class of substances, and this is nowadays generally more economical and, in some cases, also more varied and more attractive in respect of breadth of variation in structure, than the method of preparation from natural substances.

The 4-part steroid ring system is subdivided, by agreement, into the ring elements, A, B, C and D. The total chemical synthesis proceeds, from variations of sub-units, along routes of synthesis which lead to the desired target compounds of the pattern A B C D in a manner which is as efficient and simple as possible and which incorporates stereoselective and region-specific methods of carrying out reactions.

It has now been found that a total synthesis of estrone or estrone derivatives is possible in accordance with the following route:

A + D → AD → ABCD

The invention relates, therefore, to a process for the preparation of estrone or estrone derivatives which comprises reacting the aldehyde of the formula 6

 (6)

with the Grignard compound formed from 1-bromovinyltrimethylsilane to give the compound of the formula 8

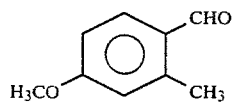 (8)

oxidizing the latter to give the compound of the formula 11

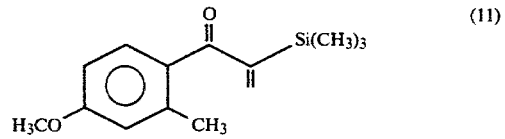 (11)

(the ring A structural unit), reacting compound 11, by a Michael reaction catalyzed by alkali metal and alkaline earth metal alcoholates, with the compound of the formula 12 c

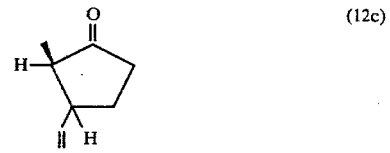 (12c)

(the ring D structural unit) (which has been obtained by reacting 2-vinylcyclopropane-1,1-dicarboxylic acid dimethyl ester of the formula 7

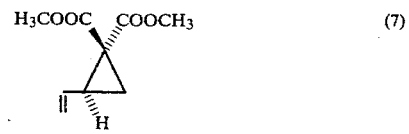 (7)

with methylmalonic acid dimethyl ester, via the cyclopentanone derivative of the formula 10

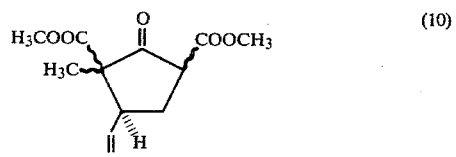 (10)

and subsequent hydrolysis and decarboxylation) to give the compound of the formula 9

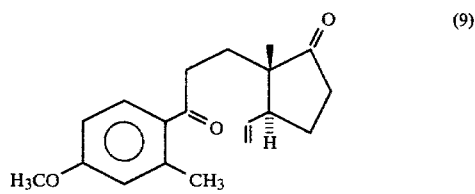 (9)

(the ring AD structural unit), and irradiating the compound of the formula 9 with UV light of a wavelength >340 nm in the presence of hydrocarbons and with the addition of pyridine/mesitol, whereupon the short-life o-quinodimethane derivative thus formed, of the formula 5

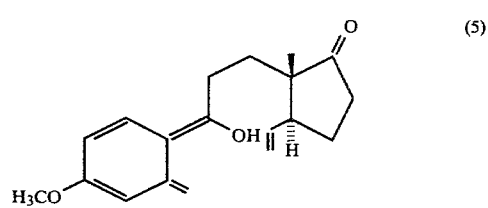 (5)

under the conditions of irradiation gives, in a stereospecific and region-specific reaction, the 9-α-hydroxyestrone 3-methyl ether of the formula 3

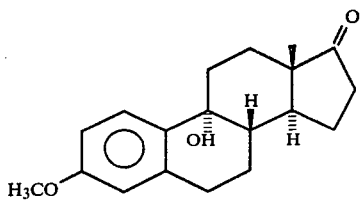
(3)

which is then converted by dehydration into 9(11)-dehydroestrone 3-methyl ether of the formula 2

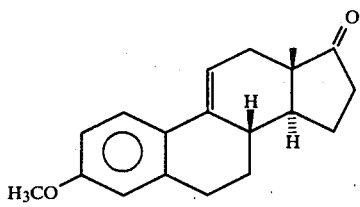
(2)

which, if desired, is converted by catalytic hydrogenation into estrone methyl ether of the formula 1

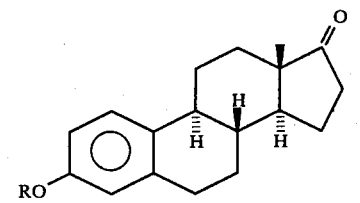
(1)

(R=CH$_3$) and, if desired, is converted into estrone of the same formula but wherein R=H.

The new total synthesis of estrone includes an asymmetric or enantiomeric synthesis of estrone or estrone derivatives which has surprisingly high yields of the desired optical isomers in the individual reaction stages if chiral starting materials are employed. It exhibits a number of surprising reaction paths and facts:

It was not to be expected that UV irradiation of the AD intermediate structural unit 9, having the BC ring open, would forthwith, and in good yields (about 60%), give the completely assembled ABCD end product 9-α-hydroxyestrone 3-methyl ether (formula 3) as the sole principal product in a so-called optical "one-pot reaction" and, in practice, in a strictly stereospecific and region-specific reaction. This fact is unique amongst all the total syntheses of estrogen known up to the present time.

Furthermore, the course of the reaction leading to the individual structural units 11 and 12 c, which are required for the synthesis of the AD structural unit 9, from the respective starting compounds 4 or 6 and 7, is peculiar and is fundamental to the invention.

The synthesis of estrone (formula 1; R=H) is effected in accordance with the synthesis route A+D→AD-→ABCD. The following reaction diagrams and the description are intended to illustrate the synthesis further. 1.1. The o-quinodimethane derivative (compound) 5 reacts by intramolecular 4+2-cycloaddition to give compound 3. The latter is converted by dehydration and catalytic hydrogenation into 1 (R=CH$_3$). The AD product 9 functions as a key compound and, by a photoenolization process, gives 5, which is kinetically unstable. Its synthesis is effected by convergent routes from the readily accessible educt components 4 or 6 and 7, respectively (R=CH$_3$).

Reaction Diagram 1

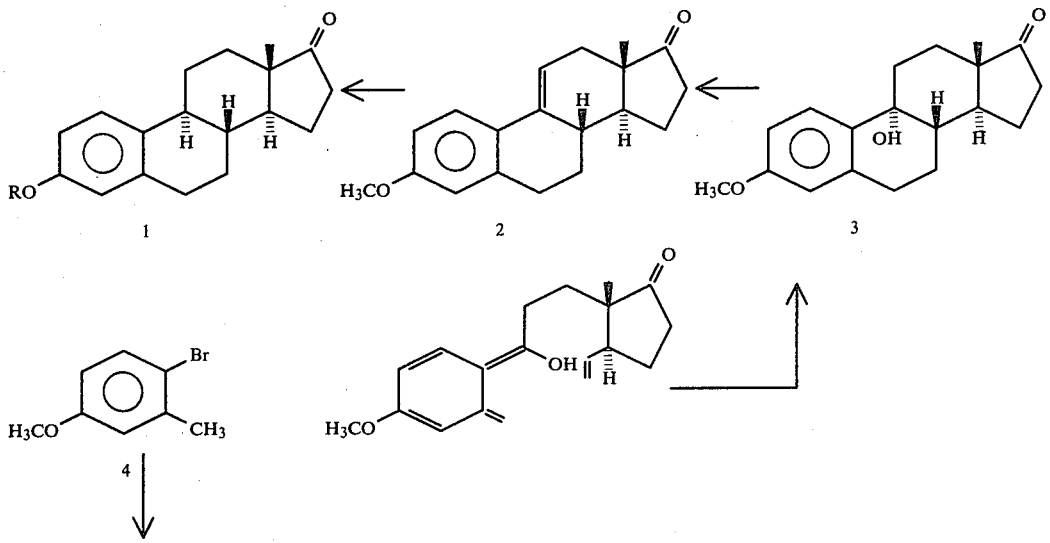

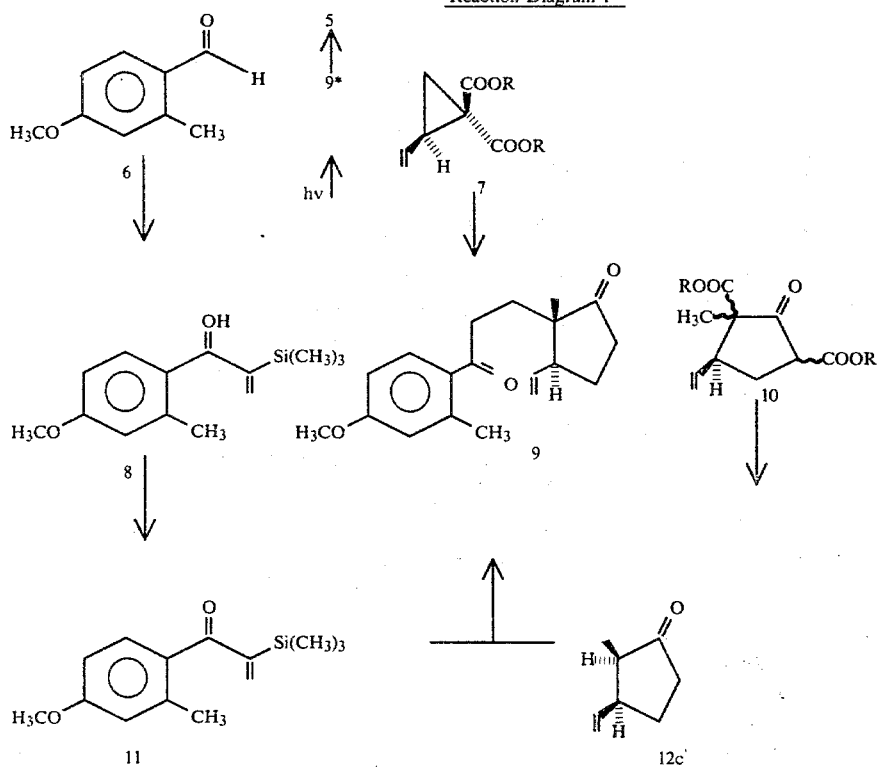

1.2. Synthesis of the ring A structural unit 11 (see Reaction Diagram 2)

Reaction Diagram 2 shows the preparation of 11.

The thick arrows emphasize the synthesis route which is finally preferred.

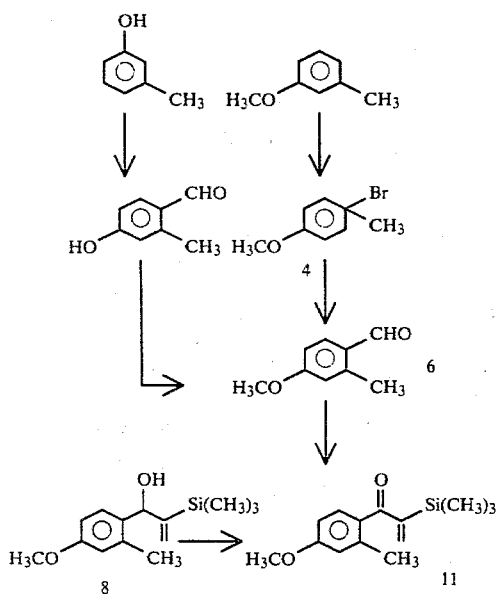

The methyl ether of m-cresol (accessible from the phenol in a yield of 80% by reaction of dimethyl sulfate on an aqueous alkaline solution of the latter) reacts with bromine in $CCl_4$ at temperatures $<0°$ C. (in the presence of iron powder) to give 4 (yield $>90\%$). The Grignard compound which is obtained in situ from 4 reacts with dimethylformamide in ether at temperatures $<-20°$ C. to give 6 (70%). The aldehyde 6 is converted into 8 (97% yield) by reacting it, at approx. 50° C. in tetrahydrofuran, with the Grignard compound obtained from 1-bromovinyltrimethylsilane. 11 is formed (80% yield) by a Jones oxidation reaction.

1.3. Synthesis of the ring D structural unit 12 (see Reaction Diagram 3)

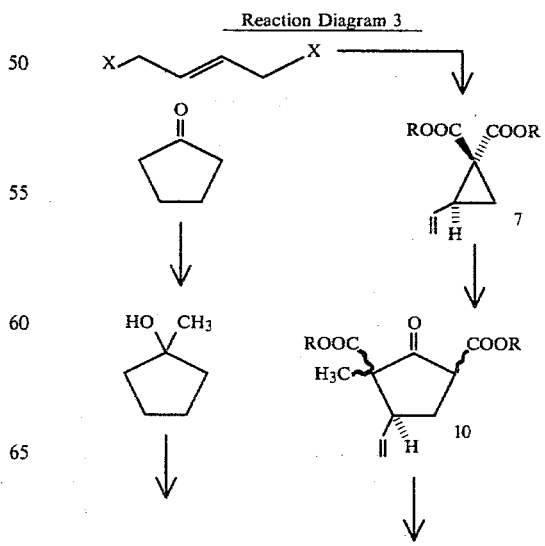

-continued
Reaction Diagram 3

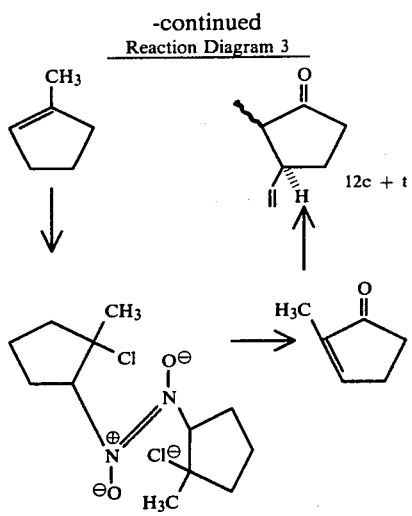

Reaction Diagram 3 shows the steps taken in order to prepare 12. The thick arrows emphasize the preferred synthesis route.

2-Vinylcyclopropane-1,1-dicarboxylic acid dimethyl ester 7, which can be obtained conveniently (yield approx. 60%) by reacting malonic acid dimethyl ester with (E)1,4-dichlorobutene in methanol containing sodium methylate at 55° C., gives the cyclopentanone derivative 10 (yield approx. 65%) when reacted with methylmalonic acid dimethyl ester in methanol solution (to which hexamethylphosphonic acid triamide has been added) containing sodium methylate. After hydrolysis (boiling for 10 hours under reflux in aqueous methanolic sodium hydroxide solution) and decarboxylation at pH 5, the mixture of stereoisomers gives the ring D structural unit (12 c+12 t=5.95) (yield approx. 70%).

7 (R) [α]$_D$= +55.0, is accessible from 7 (RS) (R=H or CH$_3$), by resolving the racemate by means of brucine. An asymmetric synthesis of 7 can be carried out as follows: malonic acid diester of the formula

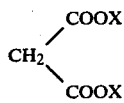

wherein O-X represents an optically active alcohol radical, preferably a radical of the formula

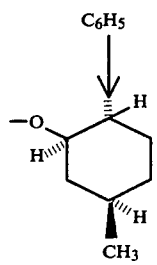

is reacted with 1,4-dichlorobutene (=diastereoselective cyclopropanation); subsequent hydrolysis and esterification with diazomethane gives optionally active 7 (R), [α]$_D$=43.9 (CCl$_4$).

1.4. Synthesis and cyclization of the AD structural unit 9 (see Reaction Diagram 1)

The educt components 11 and 12 are dissolved in t-butanol together with Na t-butylate and are reacted at room temperature to give 9 (yield approx. 60% relative to 11 or to 12). Irradiating a methylcyclohexane solution containing the Michael adduct 9, pyridine (7 molar equivalents) and mesitol (8 molar equivalents) at 95° C. with UV light of a wavelength >340 nm, for 12 hours gives a reaction product consisting mainly of 3. After it has been freed from solvent, the crude product is taken up in benzene and the solution is boiled under reflux for 20 minutes after adding oxalic acid (10 molar equivalents). A dehydration product (60% yield, relative to 9) which consists mainly of 2 and to a minor extent (approx. 5%) of 8,9-dehydroestrone methyl ether, is isolated by preparative high-pressure liquid chromatography.

The estrogens or estrogen derivatives which can be obtained by the process according to the invention have the same uses as those obtainable by other routes. Examples of fields of use have already been mentioned in the introduction to the description.

EXAMPLE 1

Synthesis of the racemic compound:

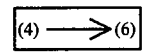

150 mmoles of (4) in 150 ml of ether are added dropwise, at boiling temperature, to 160 mmoles of Mg in 150 ml of ether and the mixture is boiled under reflux for 1 hour. 458 mmoles of HCON(CH$_3$)$_2$ in 50 ml of ether are then added dropwise at −40° C. in the course of 1.5 hours and the mixture is stirred for 2 hours (temperature rises to −20° C.); distillation in vacuo gives a 75% yield of (6).

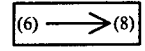

452 mmoles of 1-bromovinyltrimethylsilane [1*] in 100 ml of tetrahydrofuran are added dropwise to 452 mmoles of Mg in 200 ml of THP at a temperature below 50° C. and the mixture is stirred for 30 minutes. 273 mmoles of (6) in 100 ml of ether are then added at a temperature between 5° and 10° C. and the mixture is stirred for 12 hours to give (8) (yield of crude material 97%; analytical sample purified by preparative column chromatography (4:1 mixture of benzene and ethyl acetate)).

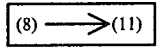

100 ml of Jones reagent solution [2*] are added dropwise at a temperature below 10° C. to 268 mmoles of (8) in 1 l of ether and the mixture is stirred for 15 hours at room temperature, to give (11; R=CH$_3$) (yield 80% after distillation in vacuo).

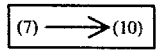

205 mmoles of methylmalonic acid dimethyl ester in 20 ml of methanol are added dropwise to a solution of 217.5 mmoles of NaOCH3 in 125 ml of methanol. After stirring for 10 minutes at 50° C., 200 mmoles of (7; R=CH3) in 25 ml of hexamethylphosphoric acid triamide and 20 ml of methanol are added. The mixture is concentrated nearly to dryness (bath temperature 100°-110° C.) in the course of 1.5 hours. After partitioning the reaction material for 8 hours between 250 ml of ether and 250 ml of 10 percent strength aqueous H2SO4, (10; R=CH3) is obtained in 67% yield (after distillation in vacuo; spinning band column).

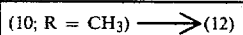

72.4 mmoles of (10; R=CH3) in 50 ml of methanol are added to 260 mmoles of NaOH in 250 ml of water, the mixture is kept at room temperature for 12 hours and then boiled under reflux for 10 hours. It is neutralized with concentrated hydrochloric acid (to bromothymol blue) and treated with NaH2PO4.2H2O for 2 hours. After 4 hours, the mixture is extracted with pentane and distillation of the extract in a bulb tube gives a 76% yield of (12c) and (12t) (5:95, according to gas chromatography).

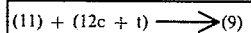

8 ml of 0.1 N NaOC(CH3)3 in HOC(CH3)3 were added dropwise in the course of 1 hour, while stirring and at room temperature, to 20.0 mmoles of (11) and 30.2 mmoles of (12c+t) in 200 ml of ether. After 12 hours the mixture was poured into 200 ml of 10 percent strength aqueous H2SO4 and 50 ml of methanol and the resulting mixture was stirred for 48 hours. After bulb tube distillation in vacuo, preparative high-pressure liquid chromatography. (10:2 petroleum ether/ethyl acetate; 2 Waters silica cartridges. 0.15 l/minute; recycled once) and bulb tube distillation. 12.9 mmoles of (9) were isolated [yield 64.5% relative to (11)]

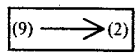

1.72 mmoles of (9), 14.7 mmoles of mesitol and 12.5 mmoles of pyridine in 450 ml of methylcyclohexane are irradiated for 12 hours at 98° C. in a Rayonet reactor (3,500 Å lamp set; wavelength range <340 nm removed by filter), while passing nitrogen through the mixture. The dried crude product from irradiation is taken up in 300 ml of benzene and boiled under reflux for 20 minutes after adding 16.7 mmoles of oxalic acid. This gives (2) [yield 54%, relative to (9)] after preparative high pressure liquid chromatography (10:2 petroleum ether-/ethyl acetate; 2 Waters silica cartridges, 0.1 l/minute; recycled twice).

[1*] A. Ottolenghi, M. Fridkin and A. Zilkha, Canad. J. Chem. 41, 2977 (1963)

[2*] K. Bowden, I. M. Heilbronn, E. R. H. Jones and B. C. L. Weedon, J. Chem. Soc. 1946, 39

Characterization of the compounds (1; R=CH3)

Melting point 142°-144° C. (from methanol). UV (methanol):$\lambda_{max}$. ($\epsilon$) 276 (1,900) and 286 nm (2,000). IR (KBr): 1,735 (s, 5-ring ketone, 1,610, 1,580 and 1,505 cm$^{-1}$ (m, w or m, benzene ring). $^1$H NMR (CDCl3): $\delta$=0.90 (s, 3H, CH3 on C), 1.23–3.10 (m, 15H, methylene and methine protons on the steroid skeleton), 3.77 (s, 3H, CH3 on 0), 6.58–6.83 and also 7.07–7.30 (in each case m; 2H or 1H of the ring A). $^{13}$C NMR (CDCl3) $\delta$=13.78 (q, C 18), 21.51 (t, C 15), 25.93 (t, C 11), 26.52 (t, C 7), 29.64 (t, C 6), 31.59 (t, C 12), 35.74 (t, C 16), 38.34 (d, C 8), 43.93 (d, C 9), 47.90 (s, C 13), 50.37 (d, C 14), 55.05 (q, OCH3), 111.52 (d, C 2), 113.86 (d, C 4), 126.21 (d, C 1), 131.93 (s, C 10), 137.58 (s, C 5), 157.60 (s, C 3) and 220.38 (s, C 17).

(2)

Melting point 150°-152° C. (from methanol). UV (methanol):$\lambda_{max}$. ($\epsilon$)=262 (19,400), shoulder at 296 nm (3,350). IR (KBr): 3,020 (w, C=C-H), 1,740 (s, α-ring ketone), 1,620 (w, C=C), 1,610, 1,575, 1,500 cm$^{-1}$ (in each case m, benzene ring). $^1$H NMR (CDCl3):$\delta$=0.93 (s, 3H, CH3 on C), 1.23–307 (m, 12H, methylene and methine protons on the steroid skeleton), 3.78 (s, 3H, CH3 on O), 6.13 (m, 1H, 11H, 6.55–6.86 and also 7.42–7.65 (in each case m, 1H, 2H or 4H). $^{13}$C NMR (CDCl3): $\delta$=14.34 (q, C 18), 22.35 (t, C 15), 27.66 (t, C 7), 29.77 (t, C 6), 33.84 (t, C 12), 36.02 (t, C 16), 38.10 (d, C 8), 46.03 (s, C 13), 47.70 (d, C 14), 55.04 (q, OCH3), 112.65 (d, C 2), 113.27 (d, C 4), 116.53 (d, C 11), 125.22 (d, C 1), 127.00 (s, C 9), 135.30 (s, C 10), 137.30 (s, C 5), 158.53 (s, C 3) and 221.21 (s, C 17).

(3)

Melting point 172°-174° C. (from methylene chloride/ether; decomposition begins gradually above 140° C.). UV (methanol):$\lambda_{max}$. ($\epsilon$)=220 (9,100), 274 (1,690), 282 nm (1,635). IR (KBr): 3,500 (s, OH), 1,725 (5-ring ketone), 1,610, 1,580, 1,500 cm (s, m or s; benzene ring). $^1$H NMR (CDCl3): $\delta$=0.90 (s, 3H, CH3 on C 13), 1.47 (s, 1H, OH), 1.60 (m, 1H), 1.80 (m, 6H), 1.96 (m, $J_{15.15}$ 12 Hz, H 15α), 2.13 (m, 2H), 2.48 (m, 2H), 2.90 (m, 2H, H 6), 3.79 (s, 3H, CH3 on O), 6.66 (d, $J_{2.4}$=2.5 Hz, 1H, H 4), 6.76 (dd, $J_{12}$=8.7, $J_{24}$=2.7 Hz, 1H, H 2), 7.45 (d, $J_{12}$=8.9 Hz, 1H, H 1). $^{13}$C NMR (CDCl3): $\delta$=12.93 (q, C 18), 20.21 (t, C 7), 21.47 (t, C 15), 27.75 (t, C 12), 29.70 (t, C 6), 32.30 (t, C 11), 35.94 (t, C 16), 41.46 (d, C 8), 43.15 (d, C 14), 47.70 (s, C 13), 55.24 (q, CH3 on O), 69.99 (s, C 9), 112.37 (d, C 2), 114.06 (d, C 4), 126.47 (d, C 1), 134.27 (s, C 10), 138.23 (s, C 5), 158.97 (s, C 3) and 220.51 (s, C 17).

(8)

UV (cyclohexane):$\lambda_{max}$. ($\epsilon$)=233 (8,600), 278 (1,340) and 284 nm (1,290). IR (film): 3,200–3,600 (s, OH), 1,615 (s, CC double bond), 1,585 and 1,505 (m or s, benzene ring), 840 (s, Si-CH3) and 810 cm$^{-1}$ (vinylidene grouping). $^1$H NMR (CDCl3; standard: cyclohexane):—0.04 (s, 9H, CH3 on Si), 1.7 (m, 1H, OH), 2.24 (s, 3H, CH3 on C), 3.80 (s, 3H, CH3 on O), 5.50 (m, 1H, allylic H), 5.59 (m, 1H, olefinic H, in cis-position to Si ligand), 5.84 (m, 1H, olefinic H in trans-position to Si ligand), 6.73 (m, 2H, H 2 and H 4) and 7.25 (m, 1H, H 1).

(9)

Boiling point 190° C./0.2 mm Hg. UV (cyclohexane):$\lambda_{max}$. ($\epsilon$)=265 nm (16,400), shoulders at 325 (200)

and 350 nm (75). IR (film): 1,738 (s, 5-ring ketone), 1,677 (s, conjugated unsaturated ketone), 1,640 (w, CC double bond) and 1,605 and 1,570 cm$^{-1}$ (benzene ring). $^1$H NMR (CDCl$_3$): $\delta=0.91$ (s, 3H, CH$_3$ on C 13), 1.71–3.1 (m, 9H, aliphatic H), 2.53 (s, 3H, CH$_3$ on C 5), 3.84 (s, 3H, CH$_3$ on O), 5.12–5.19 (m, 2H, 2 olefinic H), 5.76–5.89 (m, 1H, 1 olefinic H), 6.76 (m, 2H, aromatic H), 7.73 (m, 1H, aromatic H). $^{13}$C NMR (CDCl$_3$): $\delta=17.4$ (q, C 18), 22.36 (q, C 6), 24.31 (t, C 12), 30.54 (t, C 15), 35.48 (t, C 11/C 16), 36.78 (t, C 16/C 11), 48.48 (d, C 14), 50.82 (s, C 13), 55.11 (q, CH$_3$ on O), 110.48 (d, C 2), 116.59 (t, C 7), 117.50 (d, C 4), 129.85 (s, C 10), 131.67 (d, C 1), 137.13 (d, C 8), 141.67 (s, C 5), 161.69 (s, C 3), 200.95 (s, C 9) and 221.36 (s, C 17).

(11)

Boiling point 105° C./0.2 mm Hg. UV (cyclohexane):$\lambda_{max}$. ($\epsilon$)=275 (8,900). IR (film): 1,648 (s, conjugated unsaturated ketone), 1,610 and 1,520 (s, or m, benzene ring), 8.40 (s, Si-CH$_3$) and 800 cm$^{-1}$ (vinylidene grouping). $^1$H NMR (CDCl$_3$): $\delta=0.21$ (s, 9H, CH$_3$ on Si), 2.45 (s, 3H, CH$_3$ on C), 3.83 (s, 3H, CH$_3$ on O), 6.06 (q, AB system, 2 olefinic H), 6.71 (dd, J=2.6 Hz, J=8.5 Hz, 1H, H 2), 6.76 (d, J=2.6 Hz, 1H, H 4) and 7.39 (d, J=8.5 Hz, 1H, H 1). (12c)

IR (film): 3,080 (m, C=CH$_2$), 1,740 (s, 5-ring ketone), 1,645 and 915 cm$^{-1}$ (C=CH$_2$). $^1$H NMR (CDCl$_3$): $\delta=0.98$ (d, J=7.6 Hz, 3H, CH$_3$), 1.85–2.00 (m, 1H, aliphatic H), 2.00–2.15 (m, 1H, aliphatic H), 2.23–2.31 (m, 2H, aliphatic H), 2.23–2.31 (m, 2H, aliphatic H), 2.36 (o simplified to q, 1H, H 13; after saturation of the signal at 0.98 ppm d, J$_{13,14}$=7.8 Hz), 2.96 (m, aliphatic H), 5.04–5.17 (m, 2H, olefinic H) and 5.61–5.78 (m, 1H, olefinic H). (12t)

IR (film): 3,800 (m, C=CH$_2$), 1,740 (s, 5-ring ketone), 1,645 and 915 cm$^{-1}$ (C=CH$_2$). $^1$H NMR (CDCl$_3$): $\delta=1.05$ (d, J=6.8 Hz, 3H, CH$_3$), 1.58–1.74 (m, 1H, aliphatic H), 1.87 (o visible as a 6-line octet, 1H, H 13) after saturation of the signal at 1.05 ppm d, J$_{13,14}$=11.7 Hz), 2.04–2.44 (m, 4H, aliphatic H), 5.04–5.20 (m, 2H, olefinic H) and 5.73–5.89 (m, 1H, olefinic H).

EXAMPLE 2

Synthesis of the (+) compound of the formula 2 (R=CH$_3$)

(4) ⟶ (6)

150 mmoles of (4) in 150 ml of ether are added dropwise, at boiling temperature, to 160 mmoles of Mg in 150 ml of ether and the mixture is boiled under reflux for 1 hour. 458 mmoles of HCON(CH$_3$)$_2$ in 50 ml of ether are then added dropwise at −40° C. in the course of 1.5 hours and the mixture is stirred for 2 hours (the temperature rising to −20° C.), to give a 75% yield of (6), after distillation in vacuo.

(6) ⟶ (8)

452 mmoles of 1-bromovinyltrimethylsilane [1*] in 100 ml of tetrahydrofuran are added dropwise at a temperature <50° C. to 452 mmoles of Mg in 200 ml of THP and the mixture is stirred for 30 minutes. 273 mmoles of (6) in 100 ml of ether are then added at a temperature between 5° and 10° C. and the mixture is stirred for 12 hours to give (8) (97% yield of crude material; analytical sample purified by preparative column chromatography (4:1 benzene/ethyl acetate)).

(8) ⟶ (11)

100 ml of Jones reagent solution [2*] are added dropwise at a temperature <10° C. to 268 mmoles of (8) in 1 l of ether; (stirring at room temperature for 15 hours gives (11); R=CH$_3$) (80% yield after distillation in vacuo).

(R)-(7) ⟶ optically active (10)

205 mmoles of methylmalonic acid dimethyl ester in 20 ml of methanol are added dropwise to a solution of 217.5 mmoles of NaOCH$_3$ in 125 ml of methanol. After stirring for 10 minutes at 50° C., 200 mmoles of (R)—(7) (R=CH$_3$, [α]$_D$+55°) in 25 ml of hexamethylphosphoric acid triamide and 20 ml of methanol are added. The mixture is concentrated nearly to dryness in the course of 1.5 hours (bath temperature 100°–110° C.). The reaction material is partitioned for 8 hours between 250 ml of ether and 250 ml of 10 percent strength aqueous H$_2$SO$_4$; to give a 67% yield of optically active (10); (R=CH$_3$) (product distilled in vacuo; spinning band column).

Optically active (10) (R = CH$_3$) ⟶ (+)-(12)c 72.4 mmoles of optically active (10) (R=CH$_3$) in 50 ml of methanol are added to 260 mmoles of NaOH in 250 ml of water; the mixture is kept at room temperature for 12 hours and is boiled under reflux for 10 hours. It is neutralized with concentrated hydrochloric acid (bromothymol blue) and treated with NaH$_2$PO$_4$.2H$_2$O for 2 hours. After 4 hours, the mixture is extracted with pentane and distillation of the extract in a bulb tube gives (+)-(12)c, which has [α]$_D$+149° (CH$_2$Cl$_2$) after recrystallization.

(11) + (+)-(12)c ⟶ (+)-(9)

8 ml of 0.1 N NaOC(CH$_3$)$_3$ in HOC(CH$_3$)$_3$ was added dropwise, in the course of 1 hour and at room temperature, to 20.0 mmoles of (11) and 30.2 mmoles of (12)c in 200 ml of ether, while stirring. After 12 hours, the mixture was poured into 200 ml of 10 percent strength aqueous H$_2$SO$_4$ and 50 ml of methanol and the resulting mixture was stirred for 48 hours. After bulb tube distillation in vacuo, preparative high pressure liquid chromatography (10:2 petroleum ether/ethyl acetate; 2 Waters silica cartridges, 0.15 l/minute; recycled once) and bulb tube distillation, 12.9 mmoles of (+)-(9) were isolated [64.5% yield relative to (11)], [α]$_D$=27.1° (CHCl$_3$).

(+)-(9) ⟶ (+)-(2)

1.72 mmoles of (+)-(9), 14.7 mmoles of mesitol and 12.5 mmoles of pyridine in 450 ml of methylcyclohexane are irradiated for 12 hours at 98° C. in a Rayonet reactor (3,500 Å lamp set; wavelength range <340 nm removed by filter) while passing nitrogen through the mixture. The crude irradiation product is dried and taken up in 300 ml of benzene, 16.7 mmoles of oxalic acid are added and the mixture is boiled under reflux for 20 minutes to give (+)-(2) [54% yield relative to (+)-(9)] after purification by preparative high pressure liquid chromatography (10:2 petroleum ether/ethyl acetate; 2 Waters silica cartridges, 0.1 l/minute; recycled twice); $[\alpha]_D+288.6°$ (dioxane). [1*] A. Ottolenghi, M. Fridkin and A. Zilkha, Canad. J. Chem. 41 2977 (1963) [2*] K. Bowden, I. M. Heilbronn, E. R. H. Jones and B. C. L. Weedon, J. Chem. Soc. 1946, 39

EXAMPLE 3

Synthesis of the (+) compound of the formula 2 (R=CH₃)

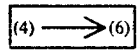

150 mmoles of (4) in 150 ml of ether are added dropwise, at boiling temperature, to 160 mmoles of Mg in 150 ml of ether and the mixture is boiled under reflux for 1 hour. 458 mmoles of HCON(CH₃)₂ in 50 ml of ether are then added dropwise at −40° C. in the course of 1.5 hours and the mixture is stirred for 2 hours (temperature rising to −20° C.) to give (6) (75% yield after distillation in vacuo).

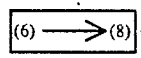

452 mmoles of 1-bromovinyltrimethylsilane [1*] in 100 ml of tetrahydrofuran are added dropwise at temperatures <50° C. to 452 mmoles of Mg in 200 ml of THP and the mixture is stirred for 30 minutes. 273 mmoles of (6) in 100 ml of ether are then added at a temperature between 5° and 10° C. and the mixture is stirred for 12 hours to give (8) (97% yield of crude material; analytical sample purified by preparative column chromatography (4:1 benzene/ethyl acetate)).

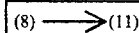

100 ml of Jones reagent solution [2*] are added dropwise at temperatures <10° C. to 268 mmoles of (8) in 1 l of ether and the mixture is stirred for 15 hours at room temperature to give (11); (R=CH₃) (80% yield after distillation in vacuo).

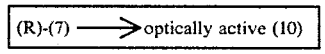

205 mmoles of methylmalonic acid dimethyl ester in 20 ml of methanol are added dropwise to a solution of 217.5 mmoles of NaOCH₃ in 125 ml of methanol. After stirring for 10 minutes at 50° C., 200 mmoles of (R)-(7), $[\alpha]_D = +43.9°$ (R=CH₃), in 25 ml of hexamethylphosphoric acid triamide and 20 ml of methanol are added. The mixture is concentrated nearly to dryness in the course of 1.5 hours (bath temperature 100°–110° C.). The reaction material is partitioned for 8 hours between 250 ml of ether and 250 ml of 10 percent strength aqueous H₂SO₄ to give a 67% yield of optically active (10) (R=CH₃) (after distillation in vacuo; spinning band column).

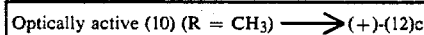

72.4 mmoles of optically active (10) (R=CH₃) in 50 ml of methanol are added to 260 mmoles of NaOH in 250 ml of water; the mixture is kept at room temperature for 12 hours and boiled under reflux for 10 hours. It is neutralized with concentrated hydrochloric acid (bromothymol blue) and treated with NaH₂PO₄.2H₂O for 2 hours. After 4 hours, the mixture is extracted with pentane and distillation of the extract in a bulb tube gives (+)-(12)c $[\alpha]_D=112.7$, yield (optical) 76%.

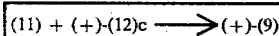

8 ml of 0.1 N NaOC(CH₃)₃ in HOC(CH₃)₃ were added dropwise, in the course of 1 hour and at room temperature, to 20.0 mmoles of (11) and 30.2 mmoles of (12)c+t in 200 ml of ether, while stirring. After 12 hours, the mixture was poured into 200 ml of 10 percent strength aqueous H₂SO₄ and 50 ml of methanol and the resulting mixture was stirred for 48 hours. After bulb tube distillation in vacuo, preparative high pressure liquid chromatography (10:2 petroleum ether/ethyl acetate; 2 Waters silica cartridges, 0.15 l/minute; recycled once) and bulb tube distillation, 12.9 mmoles of (+)-(9) were isolated [64.5% yield relative to (11)], $[\alpha]_D=21.2$, yield (optical) 80%.

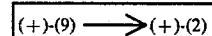

1.72 mmoles of (+)-(9), 14.7 mmoles of mesitol and 12.5 mmoles of pyridine in 450 ml of methylcyclohexane are irradiated for 12 hours at 98° C. in a Rayonet reactor (3,500 Å lamp set; wavelength range <340 nm removed by filter), while passing N₂ through the mixture. The crude irradiation product is dried and taken up in 300 ml of benzene, 16.7 mmoles of oxalic acid are added and the mixture is boiled under reflux for 20 minutes to give (+)-(2) [54% yield relative to (+)-(9)]; after preparative high pressure liquid chromatography (10:2 petroleum ether/ethyl acetate; 2 Waters silica cartridges, 0.1 l/minute; recycled twice), the product had $[\alpha]_D+231.8$; yield (optical) 80%. [1*] A. Ottolenghi, M. Fridkin and A. Zilkha, Canad. J. Chem. 41, 2977 (1963) [2*] K. Bowden, I. M. Heilbronn, E. R. H. Jones and B. C. L. Weedon, J. Chem. Soc. 1946, 39

The starting compound (R)-7, $[\alpha]_D= +43.9°$, is obtained as described on page 10; the yield (optical) is 80%, that is to say it is still contaminated by the presence of some (S)-7, which was ignored in the further course of the work.

We claim:
1. 1-(4-methoxy-2-methylphenyl)-3-(1-methyl-2-oxo-5-t-vinyl-cyclopent-r-yl)-propan-1-one.

2. A process for synthesizing 9(11)-dehydroestrone-3-methyl ether of the formula

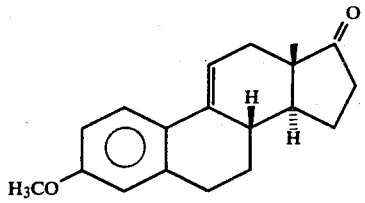

which method comprises:

reacting the aldehyde of the formula

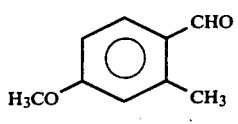

with a Grignard reagent formed between metallic magnesium and 1-bromovinyltrimethylsilane to form the compound of the formula

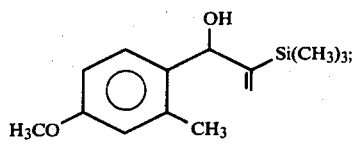

oxidizing the last-mentioned compound to form the compound of the formula

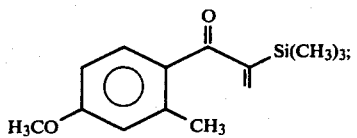

reacting the last-mentioned compound with a compound of the formula

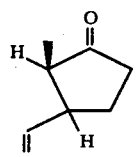

in the presence of an alkali metal alcoholate or alkaline earth metal alcoholate to form the compound of the formula

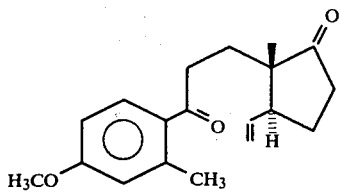

irradiating the last-mentioned compound with ultraviolet light having a wavelength longer than 340 nanometers in the presence of a hydrocarbon and pyridine/mesitol to form the short-lived intermediate o-quinodimethane compound of the formula

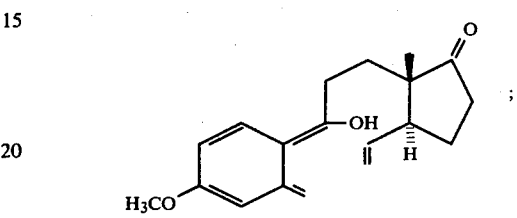

which, under the conditions of irradiation, forms 9-alpha-hydroxyestrone-3-methyl ether of the formula

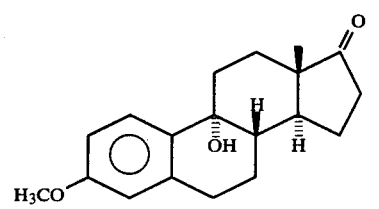

and dehydrating the last-mentioned compound into the desired 9(11)-dehydroestrone-3-methyl ether.

3. A process for making 3-vinylcyclopropan-1-one of the formula

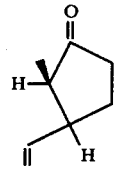

which process comprises reacting 2-vinylcyclopropane-1,1-dicarboxylic acid dimethyl ester of the formula

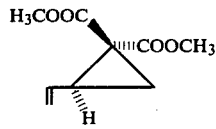

with methylmalonic acid dimethyl ester to form the cyclopentanone compound of the formula

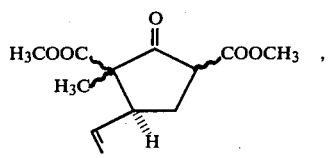

hydrolyzing the methyl ester groups to form the corresponding dicarboxylic acid, and then decarboxylating the resulting acid to form the desired compound.

* * * * *